United States Patent
Huser et al.

(10) Patent No.: US 8,719,055 B2
(45) Date of Patent: May 6, 2014

(54) METHOD AND SYSTEM TO CONTROL AND ENHANCE PRESCRIBING AND DISPENSING OF MEDICATION

(75) Inventors: Frederic J. Huser, Greenwich, CT (US); Steven B. Gold, Longboat Key, FL (US)

(73) Assignee: RX Controls, LLC, Longboat Key, FL (US)

( * ) Notice: Subject to any disclaimer, the term of this patent is extended or adjusted under 35 U.S.C. 154(b) by 151 days.

(21) Appl. No.: 12/613,262

(22) Filed: Nov. 5, 2009

(65) Prior Publication Data
US 2010/0256984 A1     Oct. 7, 2010

Related U.S. Application Data

(60) Provisional application No. 61/213,014, filed on Apr. 28, 2009, provisional application No. 61/198,322, filed on Nov. 5, 2008.

(51) Int. Cl.
*G06Q 50/24* (2012.01)
(52) U.S. Cl.
USPC ................................................. 705/3; 705/2
(58) Field of Classification Search
USPC .......................................................... 705/2–3
See application file for complete search history.

(56) References Cited

U.S. PATENT DOCUMENTS

| | | | |
|---|---|---|---|
| 5,845,255 A * | 12/1998 | Mayaud | 705/3 |
| 6,045,501 A * | 4/2000 | Elsayed et al. | 600/300 |
| 6,315,720 B1 | 11/2001 | Williams et al. | |
| 6,561,977 B2 | 5/2003 | Williams et al. | |
| 6,755,784 B2 * | 6/2004 | Williams et al. | 600/300 |
| 7,072,840 B1 | 7/2006 | Mayaud | |
| 7,304,913 B2 | 12/2007 | Niemiec et al. | |
| 7,668,730 B2 * | 2/2010 | Reardan et al. | 705/2 |
| 7,765,106 B2 * | 7/2010 | Reardan et al. | 705/2 |
| 7,765,107 B2 * | 7/2010 | Reardan et al. | 705/2 |
| 7,797,171 B2 * | 9/2010 | Reardan et al. | 705/2 |
| 2002/0032581 A1 * | 3/2002 | Reitberg | 705/2 |
| 2002/0156651 A1 | 10/2002 | Florio et al. | |
| 2002/0156653 A1 | 10/2002 | Florio et al. | |

(Continued)

FOREIGN PATENT DOCUMENTS

WO     WO 99/10829 A1     3/1999

OTHER PUBLICATIONS

D.P. Reitberg et al., "Advances in Single-Patient Trials for Drug Treatment Optimization and Risk Management," Drug Information Journal, vol. 39, pp. 119-124, 2006.*

D.P. Reitberg et al., "Advances in Single-Patient Trials for Drug Treatment Optimization and Risk Management," Drug Information Journal, vol. 39, pp. 119-124, 2005.

(Continued)

*Primary Examiner* — Michael Fuelling
(74) *Attorney, Agent, or Firm* — McDermott Will & Emery LLP

(57) ABSTRACT

Computer implemented methods and systems for controlling the dispensation of a prescription drug to a patient with a medical condition. The methods and systems may restrict the prescription and dispensation of prescription drugs at the physician and pharmacy level. Determination of whether a patient should receive a subsequent prescription of a drug is based on the effectiveness of the drug and the adverse side effects associated with the drug. This can be used by state and federal regulators, physicians and pharmacists to control, evaluate and monitor the use of drugs on an individual patient basis. Furthermore, the methods and systems provide a national registry in which drug effectiveness data in individual patients is collected which can be aggregated to provide information on population-based drug efficacy.

9 Claims, 1 Drawing Sheet

(56) References Cited

U.S. PATENT DOCUMENTS

| | | | |
|---|---|---|---|
| 2002/0192159 A1* | 12/2002 | Reitberg | 424/9.1 |
| 2004/0010511 A1 | 1/2004 | Gogolak | |
| 2004/0117126 A1* | 6/2004 | Fetterman et al. | 702/19 |
| 2005/0033606 A1 | 2/2005 | Miller | |
| 2005/0182656 A1 | 8/2005 | Morey | |
| 2005/0216307 A1 | 9/2005 | Clements et al. | |
| 2006/0018876 A1* | 1/2006 | Niklasson | 424/85.7 |
| 2006/0129433 A1 | 6/2006 | Koneru | |
| 2006/0206066 A1 | 9/2006 | Ferek-Petric | |
| 2006/0224052 A1 | 10/2006 | Williams et al. | |
| 2006/0224419 A1 | 10/2006 | Servizio et al. | |
| 2006/0271405 A1 | 11/2006 | Cipolle et al. | |
| 2007/0260491 A1 | 11/2007 | Palmer et al. | |
| 2008/0015893 A1 | 1/2008 | Miller et al. | |
| 2008/0015894 A1 | 1/2008 | Miller et al. | |
| 2008/0126131 A1 | 5/2008 | Lou | |
| 2008/0215374 A1 | 9/2008 | Craft | |
| 2008/0300719 A1* | 12/2008 | Duke | 700/244 |

OTHER PUBLICATIONS

Supplementary European Search Report issued in European Patent Application No. 09825425.3 dated Aug. 6, 2012.

Zucker, D. R., et al.: "Combining Single Patient (N-of-1) Trials to Estimate Population Treatment Effects and to Evaluate Individual Patient Responses to Treatment", J Clin Epidemiol, vol. 50, No. 4, pp. 401-410, 1997.

Sahai, Hardeo, et al.: "Pocket Dictionary of Statistics", McGraw-Hill Higher Education, 3 pages, 2000.

"Off Label Use", www.wikipedia.com, Last Viewed Dec. 17, 2013, pp. 1-8.

Gingery, Derrick: "FDA Worries About Off-Label Use, Stewardship With Limited-Population Approval Pathway", The Pink Sheet, Prescription Pharmaceuticals and Biotechnology, vol. 75, No. 6, 3 pages, Feb. 11, 2013.

Justice News: "U.S. Pharmaceutical Company Merck Sharpe & Dohme Sentenced in Connection with Unlawful Promotion of Vioxx", Department of Justice, Office of Public Affairs, 2 pages, Thursday, Apr. 19, 2012.

* cited by examiner

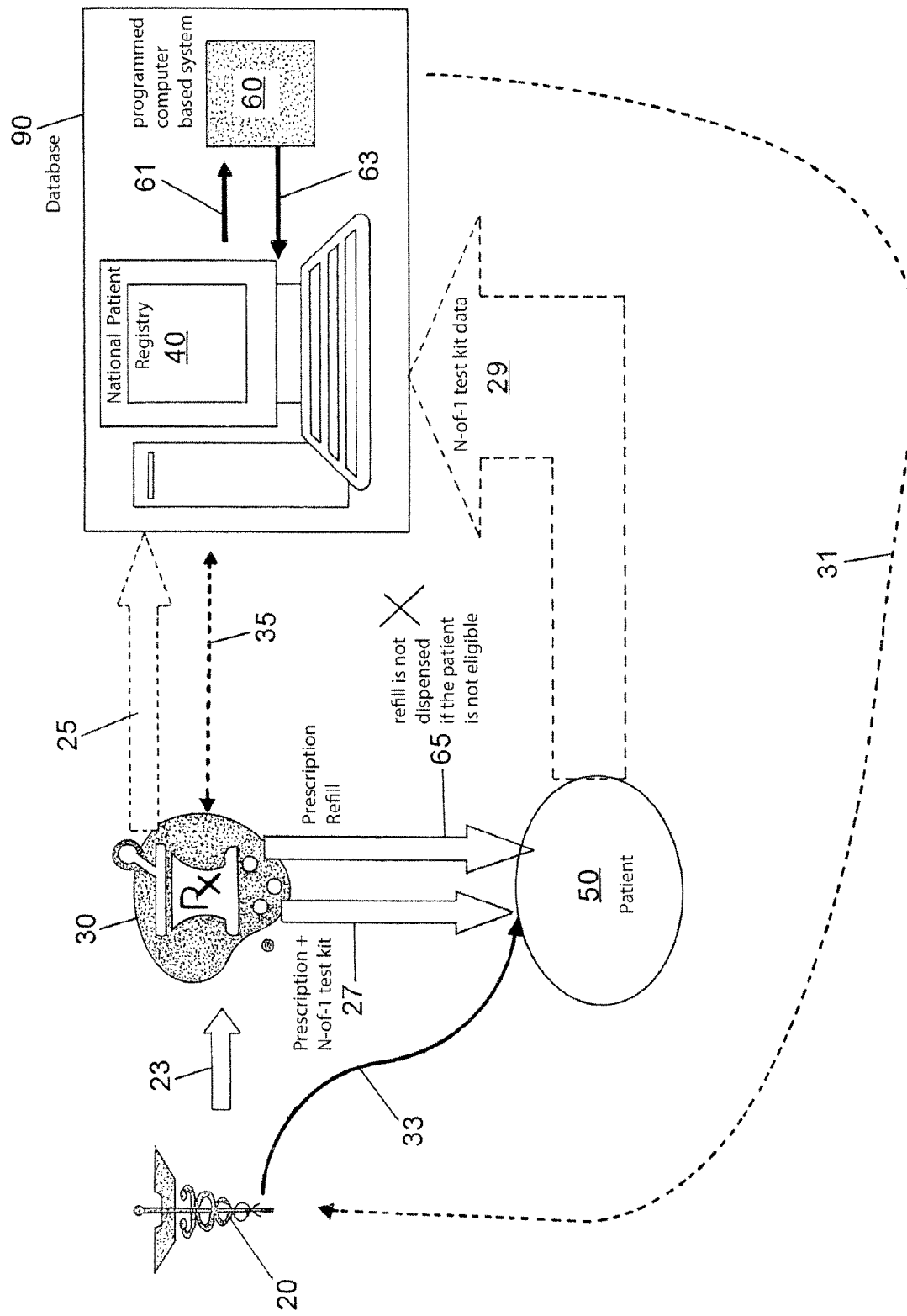

METHOD AND SYSTEM TO CONTROL AND ENHANCE PRESCRIBING AND DISPENSING OF MEDICATION

CONTINUATION DATA

This application claims priority to provisional application 61/213,014 filed on Apr. 28, 2009 and provisional application No. 61/198,322, filed on Nov. 5, 2008.

BACKGROUND

1. Technical Field

This application relates to systems and methodologies for controlling prescription and dispensation of medication.

2. Description of Related Art

The effectiveness of a prescription medication to an individual patient is uncertain prior to its administration; therefore, prescribers rely on data showing the efficacy of a particular medication on the general population to evaluate if the medication may be beneficial to an individual patient. Once the medication is prescribed and treatment is received, the effectiveness of the medication in the patient is evaluated using gross clinical observation and the prescriber cannot always determine if the prescription is having the desired effect due to false positive drug response commonly known as the placebo effect. Additionally, most if not all prescription medications are associated with side effects having varying degrees of seriousness.

One class of drugs associated with serious adverse effects ("SAE's"), is so-called "Black Box" drugs. Some drugs, while efficacious in certain individuals, are known to carry with them the potential for serious adverse side effects. Because of this potential of serious adverse effects these drugs include a black outlined box prominently displayed on the drug's prescription label, intended to emphasize the greater risk inherent in such drugs, to help physicians avoid prescribing these drugs to patients who are taking other medications that could interact unfavorably with the Black Box drug, or who have risk factors that could elevate the risk of a known adverse event occurring, and to alert the patient of such potential adverse risks.

Compounding the problem of potential SAE's of such Black Box drugs, virtually all chronic care drugs, including Black Box chronic care drugs, do not work in substantial numbers of patients. In fact, non-response and placebo response rates can be as high as 70-80% with most drugs (including Black Box drugs) averaging around 50% for placebo response and non-response. This necessarily means that large numbers of patients are exposed to drugs having potentially SAE's but for which they do not receive a true effective benefit. For those drugs that do not have the potential to cause serious adverse effects, it is of lesser concern that such tolerable adverse effects might arise. Where the known adverse effect of a Black Box drug may be of such magnitude as to indicate it not be administered in the case where there is no demonstrated benefit, there is no justification to take the risk of such adverse effect.

Conventional methods use pre-screening questionnaires to determine if the patient may be at risk for side effects associated with a drug. One known approach provides methods for avoiding adverse side effects associated with a drug based on information probative of the risk of an adverse side effect, for example the age, weight and existing health conditions of the patient.

However, despite the use of such screening methods, the adverse effects of all drugs, including Black Box drugs, generally occur randomly throughout the population and therefore, because they occur randomly, there are no salient physical or demographic characteristics that would exclude a patient from being prescribed any particular drug. It thus is impossible for doctors to screen patients from receiving the Black Box drug before the patients are exposed to it for an extended period of time. Because of the potential for serious adverse effects, it is beneficial to the patient to assure, as quickly as possible, that he or she is receiving a true and not imagined benefit, sufficient to warrant the risk inherent in such drugs.

Furthermore, state and federal regulators do not have control over dispensation of a medication prescribed for "off-label" use—that is, for treatment of a condition not indicated by the label for that medication. It has been found that the administration of drugs for such off-label uses is commonly undertaken without sufficient scientifically derived evidence of efficacy, thereby exposing the patient to unknown risks and potentially reducing the efficacy of such drugs to the population as a whole through unwarranted overuse. For these reasons as well as to manage the risks associated with unanticipated SAE's that are not revealed during the drug development process, the Food and Drug Administration has now been given enhanced statutory oversight to manage drug safety with the passage of the Food and Drug Administration Amendments Act of 2007 and, as a result, can mandate drug safety programs in connection with the approval of prescription drugs. In this regard, the Food and Drug Administration (FDA) has proposed *Guidance for Industry Format and Content of Proposed Risk Evaluation and Mitigation Strategies (REMS), REMS Assessments, and Proposed REMS Modifications* (September 2009) in which the FDA has offered the industry its guidance for such REMS including educational programs for patients and physicians or more restrictive programs that describe "safe use" conditions for certain very high risk drugs.

Therefore, a need exists for a method of evaluating the true clinical effectiveness of a black box prescription medication based on statistically valid evidence of effectiveness for its labeled indication(s) and then controlling the prescription and dispensation of the drug to only those who receive a benefit for its intended use in order to improve its risk/benefit ratio.

SUMMARY

The present subject matter is directed to methods and systems for controlling the dispensation of prescription drug refills to a patient with a medical condition. The method may comprise the steps of providing a patient with a prescription of a drug associated with efficacy in treating the medical condition; inputting data on the patient and the National Drug Code Number of the drug into a National Patient Registry database, and dispensing the prescription drug and a drug test kit to the patient. Test kit data from the patient test kit is submitted to a centralized data collection center. The patient test kit data is analyzed, indicating whether that drug in that patient resulted in indications of efficacy respecting that medical condition, and the analysis report is sent to the patient's physician. If the analysis report indicates that efficacy is present, the analysis report is entered into a national patient registry database stored on a computer-readable medium. The method then implements blocking or restricting refills of that prescription drug for that patient if the patient registry does not reflect the test kit's result of an efficacious response to that drug. Failure of the patient registry to contain that information may be the result of the patient not submitting the patient test kit results to the centralized data collection center within a predetermined period of time or if the result of the analysis of the patient data indicated no efficacious result. Through the use of succeeding patient test kits containing varying strengths of the same drug, the physician is able to determine whether the patient should receive a refill of the originally prescribed prescription drug, a modified refill of the prescription of the drug, or no refill of the prescription based on the analysis report, and control the access of the patient to such drugs through the updating of information in the patient registry.

These, as well as other components, steps, features, objects, benefits, and advantages, will now become clear from a review of the following detailed description of illustrative embodiments and the claims.

BRIEF DESCRIPTION OF DRAWINGS

FIG. 1 illustrates a method in which a pharmacy restricts dispensation of a refill prescription drug when the drug is found not to be effective in an individual patient.

DETAILED DESCRIPTION OF ILLUSTRATIVE EMBODIMENTS

Illustrative embodiments are now discussed. Other embodiments may be used in addition or instead. Details that may be apparent or unnecessary may be omitted to save space or for a more effective presentation. Conversely, some embodiments may be practiced without all of the details that are disclosed.

The present invention is generally directed to methods of and systems for controlling the dispensation of prescription drug refills to a patient with a medical condition. The methods and systems seek to control refills of prescription medication or drugs, so as to ensure that only individual patients receive the drug based on the actual effectiveness of the drug as demonstrated by that patient's own data.

The terms drugs, medication and medical therapy are used herein interchangeably. The drug is assigned by the FDA and manufacturer a National Drug Code (NDC) number for tracking and payment purposes, which is also used to identify and categorize the drug in a registry. In an embodiment of the invention, a National Patient Registry database is prepared in which a particular drug is linked by its NDC number to patient-specific effectiveness and tolerability drug response data gathered from customized or standardized N-of-1 tests.

As used herein, effectiveness is assessed in an individual patient and efficacy is assessed in the general population. The term "N-of-1" refers to the individual patient (rather than a group of subjects) being the only subject under test.

The National Patient Registry database may be stored on a central computer readable medium and may be accessed by dispensing pharmacies and medical providers. Dispensing pharmacies and medical providers may connect to the registry remotely via a terminal through existing national claims adjudication systems and data may be retrieved and submitted from and to the National Patient registry database. The present invention may be applied to various drugs, medications and medical therapies, one embodiment of which may be drugs associated with adverse side effects, such as Black Box drugs.

In an embodiment of the invention, the drug is tested with an individual patient against a placebo or the accepted standard of care in a procedure defined in the N-of-1 test. By the application of a statistical algorithm to responses provided by the individual patient, along with, in some cases objective physiological data, this N-of-1 test permits the objective determination of whether the patient is receiving a true clinical benefit from the drug, or is receiving only a placebo response, or is receiving no response at all when the drug is compared to a placebo. These data are then placed in the National Patient Registry database for electronic access and review by any pharmacist or medical provider. The pharmacist or medical provider is required to insure that the patient's data are up to date and indicate that the patient is receiving a true clinical benefit from the tested drug and dose before a refill prescription can be filled.

These N-of-1 tests are highly sensitive and specific in their ability to measure an individual's response to a particular drug, including variations in the strength of the drug prescribed. Thus, in addition to determining whether a patient receives the drug at all, the physician is able to use succeeding N-of-1 tests to modify the strength and frequency of administration of that drug in order to increase effectiveness and/or reduce the risk of adverse effects to the individual patient. Statistically, these tests can generate data that are highly certain to be accurate. That is, there is only a minor likelihood that the results seen are not real. The benefit to individual healthcare is apparent.

Once a patient is diagnosed with a particular condition, if no other suitable drugs are available, the physician may have to prescribe a drug with known adverse side effects to provide relief from the condition or to slow the progression of the disease. If such a drug is indicated, an N-of-1 test is required as a prerequisite to establishing a regimen to determine if the patient is receiving a benefit from the drug. Following the successful result of the N-of-1 test, the controlled dispensing of the drug occurs at the pharmacy level. The following process for controlling the prescribing and dispensing of the Black Box drug on an ongoing basis is established:

1. Physician writes the initial N-of-1 prescription;
2. The patient takes the prescription to a retail or mail order pharmacy;
3. Per the claims adjudication system and point of sale notification, the pharmacist is required to enter certain drug benefit plan information including the patient's name, address, employer identifiers and the National Drug Code ("NDC #") of the drug to determine reimbursement eligibility. Once these data have been entered as required, the pharmacist then dispenses an N-of-1 test kit with a specific NDC for the initial prescription. This information is then simultaneously transmitted to a national patient registry database through the claims adjudication system or other electronic methods. Note that the NDC that is maintained in the national patient registry database includes the "labeler and product codes" or the equivalent information including the manufacturer and the precise chemical formulation, strength, and dosage form. As used herein, the term "labeler" means the first 5 numeric characters of the 10-character code identifying the manufacturer or distributor and the last 5 numeric characters of the 10-character code identify the drug and the trade package size and type. The segment that identifies the drug formulation is known as the Product Code and the segment that identifies the trade package size and type is known as the Package Code.
4. Note further that that portion of the NDC representing package size or number of doses would be deleted from this information or some other mechanism used, so that the refill prescription for the same drug but in a different quantity of doses can be dispensed, permitting the physician to prescribe the appropriate number of doses of that medication without triggering the dispensing of a redundant and superfluous N-of-1 test kit.

5. The patient follows the instructions in the test kits and submits all efficacy and side effect information via electronic or paper diaries to a centralized data collection center.

6. The data are then analyzed and a report is sent to the patient's physician and entered into the national patient registry database; the data indicate that the patient either is receiving the intended benefit from the drug or is not. Alternatively, the patient registry may simply indicate the patient's identity and the particulars of the Black Box drugs for which he or she is eligible to receive. The lack of the patient's name in the patient registry along with test results from the subject drug would be sufficient to block dispensing of that drug to that patient.

7. If the patient does not submit the data before a predetermined time period, the patient registry will automatically indicate that the patient is blocked from receiving a refill prescription until the data are submitted. The predetermined time period is preferably 1 month after completion of the prescription course.

8. Based upon the data and analysis provided through the N-of-1 test, the physician then informs the patient of the test results and determines whether the patient will receive either (i) a refill prescription of the same NDC tested without regard to package size (i.e., manufacturer, strength, dosage form, and formulation) of the drug as in the original N-of-1 test, (ii) an new N-of-1 test for a modified prescription with a different NDC, or (iii) no refill.

9. In the event the physician writes a refill as in Step 7(i) above, the patient then requests the drug to be dispensed from a pharmacy. The pharmacist then checks the patient's data in the national patient registry database to determine, based on the information provided under Step 5, above, if the patient is eligible for a refill. If the data indicate a benefit, then the drug is dispensed in a manner similar to the tested drug's NDC #. The physician can prescribe the quantity determined to be appropriate so long as the NDC for labeler, strength, dosage form, and formulation are the same as originally tested).

10. In the event the physician orders a new N-of-1 test of a modified prescription as in Step 7(ii) above, the procedure beginning with Step 1 above repeats.

11. In the event the test results are negative and the physician mistakenly writes a refill, or in the event the patient goes to another physician to get another prescription, the patient will be denied the drug at the pharmacy since the patient's own data indicate that the drug is not delivering the intended benefit. (In such an event, the patient would be required to undergo a repeat of the N-of-1 test to qualify for the drug or the physician would prescribe another drug.)

The invention preferably is implemented on a hardware based system comprising a computer together with associated input/output resources, storage, and interfacing, coupled to a central database comprising the national registry or other resource via the internet, public phone lines, dedicated lines or other medium, and specifically programmed to carry out the functions described. Terminals at the sites of patients, physicians, pharmacists or other professionals or individuals involved, receive required informational inputs for analysis by data processing carried out at or in conjunction with the national patient registry. Information to be provided by the system to those involved is communicated via displays, printers, sound (speech) or other means. Exchange of information preferably is carried out in real time.

Moreover, Applicants found that an unexpected and beneficial result of the invention is the indirect control and restriction of off-label drug use. This reduces manufacturer liability by restricting the use of drugs for only labeled indications. Furthermore, the invention also has the unexpected and useful result of reducing the need for the FDA to monitor the marketplace for improper marketing of off-label usage of a drug by the pharmaceutical manufacturer, whether purposeful or not.

EXAMPLE

The following non-limiting example, which may be implemented by the described hardware system serve to provide further appreciation of the invention but are not intended to restrict the effective scope of the invention.

In this example, a dispensing pharmacy restricts dispensation of a refill prescription of a drug when the drug is not found to be effective in an individual patient.

FIG. 1 shows physician 20 diagnoses a patient 50 with a disease such as schizophrenia and prescribes 23 risperidone for treatment of the schizophrenia. Risperidone is indicated for the treatment of schizophrenia but has adverse side effects such as stroke. The patient 50 takes the prescription to a pharmacy 30 for filling of the prescription. The pharmacist enters 25 the name, social security number date of birth and any patient medical history into a database 90 comprising the National Patient Registry 40 stored on a computer readable medium along with the NDC number for the drug and dispenses 27 the prescription drug along with a patient test kit to the patient 50. The patient begins taking the drug according to the prescription directions and prior to completion of the prescription dose, submits 29 the test kit data into the centralized data collection database 90, which is subsequently sent to the National Patient Registry 40.

The test kit requires the patient to submit health information data such as symptoms. The test kit data submitted by the patient is analyzed 61 by a programmed computer-based system 60. The analysis includes comparing patient test kit data to pooled patient and historical data on the drug. An analysis report is generated 63 providing a summary indicating in this example that Risperidone is not effective in treating the individual patient's schizophrenia. The test kit data and the report are added to the National Patient Registry 40 for use in the pooled patient data. The analysis report is sent 31 to the physician electronically or via mail. If the patient does not submit the test kit data e.g., within three months, preferably within one month, and most preferably two-weeks from completion of the drug course, the patient registry will not contain that patient's name associated with the subject drug or otherwise automatically indicates that the patient is blocked from receiving a refill prescription until all data are submitted.

Based on the data and analysis report, the physician then informs 33 the patient of the test results and determines that the patient will not receive either a refill prescription of the drug (same strength and duration) or a prescription of modified specifications for the drug. Because it would be a condition of dispensing the subject drug to that particular patient that the patient's identity and the subject drug are associated in the national patient registry, the lack of the patient's identity associated with the subject drug in the patient registry would block subsequent dispensing of that drug, and no notation or other follow-up from the test to the registry alerting 35 the pharmacist not to dispense a refill prescription of the drug to the patient is required. Alternatively, a notation so alerting the pharmacist can be placed in the registry to the same effect of blocking dispensing of that prescription to that patient.

If the patient were to attempt to get a refill of the Risperidone from a different physician and take the prescription to a pharmacy, the pharmacist accesses 35 the patient's data in the National Patient Registry to determine, based on the information provided under in the analysis report which is now in the National Patient Registry, if the patient is eligible for a refill. He or she concludes that the patient is not eligible for a refill and therefore the refill is not dispensed 65.

The components, steps, features, objects, benefits and advantages that have been discussed are merely illustrative. None of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

In short, the scope of protection is limited solely by the claims that now follow. That scope is intended to be as broad as is reasonably consistent with the language that is used in the claims and to encompass all structural and functional equivalents.

The invention claimed is:

1. A method for controlling a refilling of a drug to a patient to prevent off-label use of the subject drug comprising the steps of:
   (a) receiving a prescription for the drug for the patient,
   (b) entering information on the patient and the drug into a patient registry database, wherein the drug information comprises information sufficient to identify the drug and its labeler, strength and dosage form,
   (c) dispensing the drug in an N-of-1 test kit to the patient according to the prescription,
   (d) accessing an analysis report stored in the patient registry database, wherein:
      the analysis report is generated by a computer programmed to analyze data from the N-of-1 drug test kit stored in the patient registry database, the analysis report indicating whether the patient is receiving an intended labeled benefit from the drug specified by a manufacturer of the drug and by a government agency,
   (e) receiving a prescription for a refill of the drug, and
   (f) preventing off-label use of the drug by permitting dispensation of the refill to a patient who, based on the analysis report, is receiving the intended labeled benefit from the drug and restricting dispensation of the refill to a patient who, based on the analysis report, is not receiving the intended labeled benefit from the drug, wherein there are at least two patients, and at least one of the patients is engaging in off-label use, and not receiving the intended labeled benefit from the drug, and at least one of the patients is receiving the intended labeled benefit from the drug, and wherein the test kit and drug are associated by at least one identifying code number.

2. The method of claim 1, wherein the data from the N-of-1 test kit comprises patient drug response information and side effect information.

3. The method of claim 1, wherein said analysis report is accessed electronically.

4. The method of claim 1, wherein the appropriateness of the drug is further determined by evaluating the N-of-1 test kit data for serious side effects.

5. The method of claim 1 wherein, the method is repeated if a higher or lower dose of the drug is prescribed.

6. The method of claim 1, wherein dispensation of the drug is blocked if the N-of-1 test kit data are not submitted within a predetermined time.

7. The method of claim 6, wherein the predetermined time is one month after completion of the N-of-1 prescription course.

8. The method of claim 1, wherein the patient registry database is stored on a non-transitory computer readable medium and is accessible by dispensing pharmacies.

9. The method of claim 1, wherein the drug is associated with serious side effects.

\* \* \* \* \*